United States Patent
Schumacher et al.

(10) Patent No.: US 11,592,028 B2
(45) Date of Patent: Feb. 28, 2023

(54) FLUID PUMP HAVING AT LEAST ONE IMPELLER BLADE AND A SUPPORT DEVICE

(71) Applicant: ECP ENTWICKLUNGSGESELLSCHAFT MBH, Berlin (DE)

(72) Inventors: Joerg Schumacher, Teltow (DE); Daniel Roehn, Berlin (DE)

(73) Assignee: ECP ENTWICKLUNGSGESELLSCHAFT MBH, Aachen (DE)

(*) Notice: Subject to any disclaimer, the term of this patent is extended or adjusted under 35 U.S.C. 154(b) by 1087 days.

(21) Appl. No.: 16/243,855

(22) Filed: Jan. 9, 2019

(65) Prior Publication Data
US 2019/0211836 A1 Jul. 11, 2019

Related U.S. Application Data

(63) Continuation of application No. 14/807,615, filed on Jul. 23, 2015, now Pat. No. 10,208,763, which is a (Continued)

(30) Foreign Application Priority Data

Sep. 22, 2009 (EP) ..................... 09075441

(51) Int. Cl.
*F04D 29/18* (2006.01)
*F04D 19/00* (2006.01)
(Continued)

(52) U.S. Cl.
CPC ........... *F04D 29/181* (2013.01); *F04D 19/00* (2013.01); *F04D 29/528* (2013.01);
(Continued)

(58) Field of Classification Search
CPC ...... F04D 29/181; F04D 29/528; F04D 19/00; A61M 5/14236; A61M 60/205;
(Continued)

(56) References Cited

U.S. PATENT DOCUMENTS 3,510,229 A 5/1970 Smith et al.
3,568,659 A 3/1971 Kamegis
(Continued)

FOREIGN PATENT DOCUMENTS

CA 2701809 A1 4/2009
CA 2701810 A1 4/2009
(Continued)

OTHER PUBLICATIONS

Office Action received in corresponding German Patent Application No. 11 2010 003745.0 dated May 6, 2022, (14 pp.).

*Primary Examiner* — Charles G Freay
(74) *Attorney, Agent, or Firm* — Botos Churchill IP Law LLP (57) ABSTRACT

The invention relates to a fluid pump comprising at least one impeller blade (1, 1', 1") which is rotatable about an axis of rotation (3) and conveys a fluid in operation and comprising a support device (4, 6, 7, 8, 9, 10, 12, 12', 13, 13', 14, 14', 15, 17) which supports the at least one impeller blade (1, 1', 1") in at least one support region, wherein the support device is change-able between a first state in which the rotor is radially compressed and a second state in which the rotor is radially expanded; and wherein at least one impeller blade extends at least partly radially inwardly with respect to the axis of rotation (3) from the support region/support regions in the radially expanded state of the rotor.

21 Claims, 6 Drawing Sheets

Related U.S. Application Data continuation of application No. 13/261,205, filed as application No. PCT/EP2010/005867 on Sep. 22, 2010, now Pat. No. 9,089,634.

(60) Provisional application No. 61/244,592, filed on Sep. 22, 2009.

(51) Int. Cl.

| | | |
|---|---|---|
| *F04D 29/52* | (2006.01) | |
| *A61M 5/142* | (2006.01) | |
| *A61M 60/148* | (2021.01) | |
| *A61M 60/414* | (2021.01) | |
| *A61M 60/808* | (2021.01) | |
| *A61M 60/806* | (2021.01) | |
| *A61M 60/237* | (2021.01) | |

(52) U.S. Cl.
CPC ....... *A61M 5/14236* (2013.01); *A61M 60/148* (2021.01); *A61M 60/237* (2021.01); *A61M 60/414* (2021.01); *A61M 60/806* (2021.01); *A61M 60/808* (2021.01); *A61M 2205/0244* (2013.01); *A61M 2205/0266* (2013.01)

(58) Field of Classification Search
CPC .............. A61M 60/135; A61M 60/148; A61M 60/414; A61M 60/808; A61M 2205/0244; A61M 2205/0266
See application file for complete search history.

(56) References Cited

U.S. PATENT DOCUMENTS

| | | | |
|---|---|---|---|
| 3,802,551 A | 4/1974 | Somers | |
| 3,812,812 A | 5/1974 | Hurwitz | |
| 4,014,317 A | 3/1977 | Bruno | |
| 4,207,028 A | 6/1980 | Ridder | |
| 4,559,951 A | 12/1985 | Dahl et al. | |
| 4,563,181 A | 1/1986 | Wijayarathna et al. | |
| 4,679,558 A | 7/1987 | Kensey et al. | |
| 4,686,982 A | 8/1987 | Nash | |
| 4,747,821 A | 5/1988 | Kensey et al. | |
| 4,749,376 A | 6/1988 | Kensey et al. | |
| 4,753,221 A | 6/1988 | Kensey et al. | |
| 4,801,243 A | 1/1989 | Norton | |
| 4,817,613 A | 4/1989 | Jaraczewski et al. | |
| 4,919,647 A | 4/1990 | Nash | |
| 4,957,504 A | 9/1990 | Chardack | |
| 4,969,865 A * | 11/1990 | Hwang ............... | F04D 3/00 623/3.15 |
| 4,995,857 A | 2/1991 | Arnold | |
| 5,011,469 A | 4/1991 | Buckberg et al. | |
| 5,040,944 A | 8/1991 | Cook | |
| 5,042,984 A | 8/1991 | Kensey et al. | |
| 5,052,404 A | 10/1991 | Hodgson | |
| 5,061,256 A | 10/1991 | Wampler | |
| 5,092,844 A | 3/1992 | Schwartz et al. | |
| 5,097,849 A | 3/1992 | Kensey et al. | |
| 5,108,411 A | 4/1992 | McKenzie | |
| 5,112,292 A | 5/1992 | Hwang et al. | |
| 5,113,872 A | 5/1992 | Jahrmarkt et al. | |
| 5,117,838 A | 6/1992 | Palmer et al. | |
| 5,118,264 A | 6/1992 | Smith | |
| 5,145,333 A | 9/1992 | Smith | |
| 5,163,910 A | 11/1992 | Schwartz et al. | |
| 5,169,378 A | 12/1992 | Figuera | |
| 5,183,384 A | 2/1993 | Trumbly | |
| 5,191,888 A | 3/1993 | Palmer et al. | |
| 5,192,286 A | 3/1993 | Phan et al. | |
| 5,201,679 A | 4/1993 | Velte, Jr. et al. | |
| 5,275,580 A | 1/1994 | Yamazaki | |
| 5,300,112 A | 4/1994 | Barr | |
| 5,373,619 A | 12/1994 | Fleischhacker et al. | |
| 5,376,114 A | 12/1994 | Jarvik | |
| 5,405,383 A | 4/1995 | Barr | |
| 5,501,574 A | 3/1996 | Raible | |
| 5,531,789 A | 7/1996 | Yamazaki et al. | |
| 5,676,162 A | 10/1997 | Larson, Jr. et al. | |
| 5,676,651 A | 10/1997 | Larson, Jr. et al. | |
| 5,693,091 A | 12/1997 | Larson, Jr. et al. | |
| 5,701,911 A | 12/1997 | Sasamine et al. | |
| 5,702,430 A | 12/1997 | Larson, Jr. et al. | |
| 5,722,429 A | 3/1998 | Larson, Jr. et al. | |
| 5,722,930 A | 3/1998 | Larson, Jr. et al. | |
| 5,749,855 A | 5/1998 | Reitan | |
| 5,755,784 A | 5/1998 | Jarvik | |
| 5,758,666 A | 6/1998 | Larson, Jr. et al. | |
| 5,776,190 A | 7/1998 | Jarvik | |
| 5,813,405 A | 9/1998 | Montano, Jr. et al. | |
| 5,820,571 A | 10/1998 | Erades et al. | |
| 5,843,129 A | 12/1998 | Larson, Jr. et al. | |
| 5,851,174 A | 12/1998 | Jarvik et al. | |
| 5,879,375 A | 3/1999 | Larson, Jr. et al. | |
| 5,882,329 A | 3/1999 | Patterson et al. | |
| 5,888,241 A | 3/1999 | Jarvik | |
| 5,938,672 A | 8/1999 | Nash | |
| 6,030,397 A | 2/2000 | Monetti et al. | |
| 6,129,704 A | 10/2000 | Forman et al. | |
| 6,152,693 A | 11/2000 | Olsen et al. | |
| 6,168,624 B1 | 1/2001 | Sudai | |
| 6,254,359 B1 | 7/2001 | Aber | |
| 6,302,910 B1 | 10/2001 | Yamazaki et al. | |
| 6,308,632 B1 | 10/2001 | Shaffer | |
| 6,336,939 B1 | 1/2002 | Yamazaki et al. | |
| 6,346,120 B1 | 2/2002 | Yamazaki et al. | |
| 6,387,125 B1 | 5/2002 | Yamazaki et al. | |
| 6,503,224 B1 | 1/2003 | Forman et al. | |
| 6,506,025 B1 | 1/2003 | Gharib | |
| 6,508,787 B2 | 1/2003 | Erbel et al. | |
| 6,517,315 B2 | 2/2003 | Belady | |
| 6,527,521 B2 | 3/2003 | Noda | |
| 6,533,716 B1 | 3/2003 | Schmitz-Rode et al. | |
| 6,537,030 B1 | 3/2003 | Garrison | |
| 6,537,315 B2 | 3/2003 | Yamazaki et al. | |
| 6,592,612 B1 | 7/2003 | Samson et al. | |
| 6,652,548 B2 | 11/2003 | Evans et al. | |
| 6,719,791 B1 | 4/2004 | Nusser et al. | |
| 6,790,171 B1 | 9/2004 | Grundeman et al. | |
| 6,860,713 B2 | 3/2005 | Hoover | |
| 6,945,977 B2 | 9/2005 | Demarais et al. | |
| 6,981,942 B2 | 1/2006 | Khaw et al. | |
| 7,022,100 B1 | 4/2006 | Aboul-Hosn et al. | |
| 7,027,875 B2 | 4/2006 | Siess et al. | |
| 7,074,018 B2 | 7/2006 | Chang | |
| 7,118,356 B2 | 10/2006 | Ma et al. | |
| 7,179,273 B1 | 2/2007 | Palmer et al. | |
| 7,393,181 B2 | 7/2008 | McBride et al. | |
| 7,467,929 B2 | 12/2008 | Nusser et al. | |
| 7,731,675 B2 | 6/2010 | Aboul-Hosn et al. | |
| 7,798,952 B2 | 9/2010 | Tansley et al. | |
| 7,841,976 B2 * | 11/2010 | McBride ............... | F04D 29/247 416/240 |
| 7,927,068 B2 | 4/2011 | McBride et al. | |
| 7,934,909 B2 | 5/2011 | Nuesser et al. | |
| 7,942,804 B2 | 5/2011 | Khaw | |
| 8,012,079 B2 | 9/2011 | Delgado, III | |
| 8,177,703 B2 | 5/2012 | Smith et al. | |
| 8,366,411 B2 | 2/2013 | Baykut et al. | |
| 8,376,707 B2 | 2/2013 | McBride et al. | |
| 8,617,239 B2 | 12/2013 | Reitan | |
| 8,641,594 B2 | 2/2014 | LaRose et al. | |
| 8,734,331 B2 * | 5/2014 | Evans ................... | A61M 60/13 600/116 |
| 8,979,493 B2 * | 3/2015 | Roehn ................. | A61M 60/205 416/88 |
| 9,028,216 B2 * | 5/2015 | Schumacher ......... | F04D 29/181 416/176 |
| 9,089,634 B2 * | 7/2015 | Schumacher ..... | A61M 5/14236 |
| 10,208,763 B2 * | 2/2019 | Schumacher ..... | A61M 5/14236 |
| 11,291,824 B2 * | 4/2022 | Schwammenthal ........................ | A61M 60/585 |
| 2002/0010487 A1 * | 1/2002 | Evans ................... | A61B 17/221 606/159 |

(56) References Cited

U.S. PATENT DOCUMENTS

| | | |
|---|---|---|
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | krivoruchko |
| 2004/0215228 A1 | 10/2004 | Simpson et al. |
| 2005/0017603 A1 | 1/2005 | Ma et al. |
| 2005/0227277 A1 | 10/2005 | Tang et al. |
| 2006/0008349 A1 | 1/2006 | Khaw |
| 2006/0036127 A1 | 2/2006 | Delgado |
| 2006/0062672 A1 | 3/2006 | McBride et al. |
| 2006/0195004 A1 | 8/2006 | Jarvik |
| 2006/0276880 A1* | 12/2006 | Neuss ............... A61F 2/915 623/1.15 |
| 2007/0112033 A1 | 5/2007 | Trieselmann et al. |
| 2007/0156006 A1* | 7/2007 | Smith ............... A61M 60/422 600/16 |
| 2007/0276480 A1 | 11/2007 | Tansley et al. |
| 2008/0103591 A1 | 5/2008 | Siess |
| 2008/0132747 A1* | 6/2008 | Shifflette ......... A61M 60/414 600/16 |
| 2008/0262584 A1 | 10/2008 | Bottomley et al. |
| 2008/0292478 A1 | 11/2008 | Baykut et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2009/0112312 A1 | 4/2009 | LaRose et al. |
| 2010/0041939 A1 | 2/2010 | Siess |
| 2010/0172741 A1* | 7/2010 | Hosoya ............. F04D 29/665 415/206 |
| 2010/0268017 A1 | 10/2010 | Siess |
| 2011/0071338 A1 | 3/2011 | McBride et al. |
| 2011/0152999 A1* | 6/2011 | Hastings ............ A61M 60/419 623/1.15 |
| 2011/0236210 A1 | 9/2011 | McBride et al. |
| 2011/0238172 A1 | 9/2011 | Akdis |
| 2011/0275884 A1 | 11/2011 | Scheckel |
| 2012/0029265 A1 | 2/2012 | LaRose et al. |
| 2012/0039711 A1 | 2/2012 | Roehn |
| 2012/0041254 A1* | 2/2012 | Scheckel ............ A61M 60/205 600/16 |
| 2012/0041255 A1 | 2/2012 | Delgado, III |
| 2012/0046648 A1 | 2/2012 | Scheckel |
| 2012/0059460 A1 | 3/2012 | Reitan |
| 2012/0093628 A1 | 4/2012 | Liebing |
| 2012/0101455 A1 | 4/2012 | Liebing |
| 2012/0142994 A1 | 6/2012 | Foellner |
| 2012/0184803 A1 | 7/2012 | Simon et al. |
| 2012/0224970 A1 | 9/2012 | Schumacher et al. |
| 2012/0226097 A1 | 9/2012 | Smith et al. |
| 2012/0234411 A1 | 9/2012 | Scheckel |
| 2012/0237353 A1 | 9/2012 | Schumacher et al. |
| 2012/0237357 A1* | 9/2012 | Schumacher ......... F04D 29/247 416/234 |
| 2012/0245404 A1 | 9/2012 | Smith et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0129503 A1 | 5/2013 | McBride et al. |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |
| 2014/0148638 A1 | 5/2014 | LaRose et al. |

FOREIGN PATENT DOCUMENTS

| | | |
|---|---|---|
| CN | 114432588 A * | 5/2022 |
| EP | 1738783 A1 | 1/2007 |
| EP | 2047872 A1 | 4/2009 |
| GB | 2239675 A | 7/1991 |
| WO | 9853864 A1 | 12/1998 |
| WO | 2003103745 A2 | 12/2003 |
| WO | 2007112033 A2 | 10/2007 |

* cited by examiner

FLUID PUMP HAVING AT LEAST ONE IMPELLER BLADE AND A SUPPORT DEVICE

CROSS REFERENCE TO RELATED APPLICATIONS

This application is a continuation of U.S. patent application Ser. No. 14/807,615, filed Jul. 23, 2015 (now U.S. Pat. No. 10,208,763), which is a continuation of U.S. application Ser. No. 13/261,205, filed May 16, 2012 (now U.S. Pat. No. 9,089,634), which is a national stage filing under 35 U.S.C. § 371 of International Application No. PCT/EP2010/005867, filed Sep. 22, 2010, which claims the benefit of U.S. Provisional Application No. 61/244,592, filed Sep. 22, 2009, and European Application No. 09075441.7, filed Sep. 22, 2009. The disclosures of each of the foregoing applications are hereby incorporated by reference in their entirety. International Application No. PCT/EP2010/005867 was published under PCT Article 21(2) in English.

The invention is in the field of mechanical engineering, in particular micromechanics, and addresses fluid pumps which work with rotating impeller blades and are particularly configured for use in areas which are difficult to access.

Pumps of this type can be used, for example, in the medical field and can also have particularly small construction shapes for this purpose.

A special application of micropumps is, for example, the assistance for the pump force of the human heart. Pumps used in this area are usually introduced into the body through blood vessels and are optionally operated in a chamber of the heart.

A plurality of such pumps have already become known which have different constructional shapes. An axial flow pump has become known, from WO 98/53864, and equally from EP 1 738 783 A1, which in each case has a rotor in the form of a rigid shaft, said rotor being provided with impeller blades and said shaft being outwardly journalled in a stator. The drive can be directly integrated into the stator and the rotor as an electromagnetic drive.

Pumps of this type have the disadvantage that they have a large diameter in relation to the pumping capacity and can hardly be introduced through a blood vessel.

In contrast to this, a rotor is known from WO 03/013745 A2 which has a smaller diameter in a compressed state than in an expanded state and which has an expandable rotor blade which expands in operation by the fluid counterpressure of the blood.

Other rotors which have become known likewise have impeller blades which are expandable for operation, for example by joints or by elastic deformability of the impeller blades.

A particular problem in this respect is that the impeller blades are usually fastened to a central neck and are rotationally drivable and also movably pivotable from this; that the impeller blades thus have to be flexible, but have a certain stiffness or a restriction in its movability, on the other hand, to exert the required pressure onto the fluid for conveying.

This object has previously not been ideally achieved in the prior art. It is therefore the underlying object of the present invention to further develop a pump of the described type to achieve a good pumping capacity in operation despite a small pump diameter in the compressed state. The design should in this respect be as uncomplicated and as inexpensive as possible.

The object is achieved in accordance with the invention by the features of the claims.

In this respect, at least one impeller blade is provided which is rotatable about an axis of rotation to convey the fluid as well as support device which supports the at least one impeller blade in a support region. The support device is moreover changeable between a compressed rotor state and an expanded rotor state and at least one part of at least one impeller blade extends at least partly, viewed from the support region, radially inwardly toward the rotor axis in the expanded rotor state. Since the support region is not disposed at the radially inner end of the impeller blade, but is rather offset to the impeller blade exterior, viewed radially, the impeller blade/impeller blades is/are supported in a region in which the relative speed to the fluid is greater than in the region of the axis of rotation and, where applicable, the mechanical load of the impeller blade is correspondingly higher. The support region and the support device can be the only region in which the impeller blade/impeller blades is/are journalled or is/are connected to another component. The impeller blade/impeller blades can, for example, be connected to other components in a force-transmitting manner only by means of the support device. In this respect, the region of the impeller blade/impeller blades conveying the fluid can lie wholly or only partly radially within the support region. A lower mechanical demand is in any case made here on the support device and on its connection to the respective impeller blade than if the support device were to support the impeller blades in the region of the axis of rotation. The impeller blades can moreover be made weaker since they are supported in a region of higher load and the mean spacing of the regions of the impeller blade/impeller blades conveying the fluid, viewed in the radial direction, is smaller than if it/they were supported in the region of a neck on the axis of rotation.

The support device can have a strand-like body which extends transversely to the impeller blade surface with respect to its longitudinal direction and/or, in the region in which it supports the impeller blade, passes through said impeller blade or a tangential surface of said impeller blade. The angle between the longitudinal direction of the strand-like body and of the surface normal of the impeller blade surface/of the tangential surface at the impeller blade surface should be less than 89°, preferably less than 85°.

Provision can also be made that the predominant part of the region of the impeller blade/impeller blades conveying the fluid extends radially within the support region/support regions. The support region is thus closer to the parts of the impeller blade/impeller blades which move the fastest and can support them efficiently, for example transmit a torque to them.

Provision can advantageously also be made that the support region is arranged radially outwardly at the periphery of the fluid-conducting region of the impeller blade/impeller blades. In this respect, the support region can completely radially outwardly surround the impeller blades.

The impeller blade can generally be fixedly connected to the support device so that it rotates with the impeller blade.

This is a construction shape which can be manufactured particularly simply and which is mechanically stable. The support device can, for example, comprise the same material as the impeller blade and can be manufactured in one piece therewith.

Provision can, however, also be made that the support device is manufactured from a material different from that of the impeller blade, for example from a superelastic compound or from a shape memory material, in particular nitinol, so that the support device can actively change into an operating shape in order thus to erect the rotor with the impeller blades so that no further demands are made on the impeller blades with respect to an automatic deformation. They can then be manufactured as thin, pliable films which are not self-supporting.

The at least one impeller blade can, however, also be guided and journalled movably with respect to the support device. The support device can then he stationary with respect to the impeller blades as a stator. A guidance, for example in the form of a mechanical or magnetic journaling of the impeller blades with respect to the support device is then necessary.

The support device can, for example, be formed by at least one ring positioned concentrically and optionally journaled with respect to the axis of rotation. This ring can have an axial length which is smaller than the axial length of the impeller blades.

Two or more such rings can also respectively be connected, axially spaced apart, to the impeller blade/impeller blades. The rings can be designed in meandering form in the peripheral direction, for example, to be able to implement a corresponding deformability, for example as a consequence of superelasticity or shape memory properties in a particularly simple manner. A plurality of rings are preferably arranged coaxially to one another.

Figure 15:
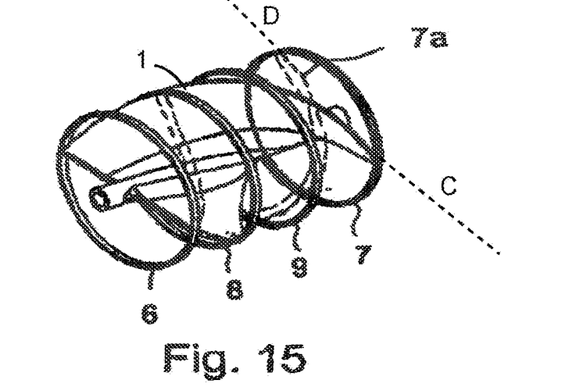
FIG. 15 a rotor with a support device having four rings in a three-dimensional view.

As shown in FIG. 15, a helical body 7a can also be provided coaxial to the axis of rotation as a support body instead of one or more rings. It can, for example, have a round or flat cross-section. The helix can extend in the same direction 'C' or in the opposite direction 'D' to a helical outer margin of an impeller blade 1.

The support device can, however, also be formed by a flexible tube surrounding the impeller blade/impeller blades. Such a tube can itself comprise a shape memory material, for example, also a wire meshwork of nitinol wire or it can comprise a flexible organic material impermeable for the fluid and have support elements such as support rings, for example. The tube can be inflatable in pumping operation by overpressure as a result of the fluid pressure which has built up.

The tube can be connected at points or in parts to the outer ends of the impeller blade/impeller blades.

In accordance with the present invention, the rotor does not need a neck in the region of the impeller blades so that the impeller blade/impeller blades, with all its/their parts, can be spaced apart from the axis of rotation. In this case, the cross-section of the rotor, which is otherwise taken up by a neck, is additionally available for conveying fluid.

When the support device rotates with the impeller blade/impeller blades, it can be journalled in at least one rotary bearing which is axially arranged outside the region over which the impeller blade/impeller blades extends/extend.

This design allows a simple journalling in a commercial rotary bearing, for example a roller bearing or a magnetic bearing. Such a journalling is less complicated and lower in friction than a journalling at the periphery of the support device in the region of the impeller blades.

However, a hydrodynamic journalling can, for example, also be provided at the periphery of the support device when a rotor of the described kind runs in a housing and when a gap is provided between the housing and the support device in which a fluid is located. In a particularly simple embodiment, this fluid could be identical with the conveyed fluid.

The invention will be shown and subsequently described in the following with reference to an embodiment in a drawing. There are shown FIG. 1 a three-dimensional, partly broken away view of a rotor of a fluid pump with a support device and an impeller blade;

FIG. 2 an axial plan view of the subject of FIG. 1;

Figures 1, 2:
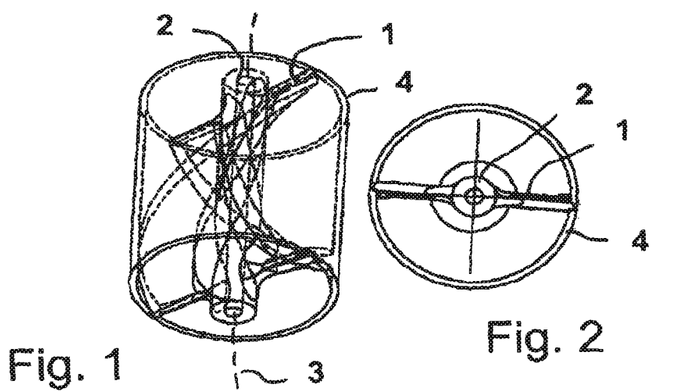

FIG. 1 shows, in a three-dimensional view, a rotor of a fluid pump, in particular of a micropump, for the axial conveying of blood, such as is typically used in medicine to assist the human heart. Such a pump is, for example, mounted at the end of a hollow catheter and conducts blood under pressure from a chamber of the heart into a blood vessel when it is introduced into a heart ventricle through a blood vessel. For this purpose, a rotor rotates at some thousand revolutions per minute to achieve the required conveying capacity. The impeller blade 1 is helical in form, is connected to a neck 2 in the region of the axis of rotation 3 and is supported outwardly by a support device 4 in the form of a tubular sleeve, to which the impeller blade 1 is connected at its outer margin.

The neck 2 is typically connected to a drivable shaft which extends through the hollow catheter and blood vessel to a motor drive which can typically be arranged outside the body. A sluice is provided between the motor drive and the hollow catheter.

FIG. 2 shows a plan view in which the upper margin of the impeller blade 1 and the tubular sleeve 4 can easily be recognized.

The impeller blade 1 can also be understood as two partial impeller blades which extend respectively radially from the neck 2 to the tubular support device 4 and axially extend helically.

Figure 3:
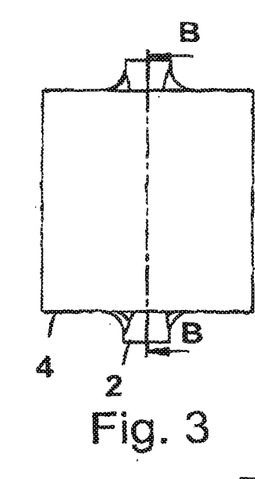
FIG. 3 a side view

FIG. 3 shows the rotor from FIG. 1 in a side view, with the closed pipe-like or tubular sleeve 4 being easy to recognize and the ends of the neck 2 projecting beyond it.

Figure 4:
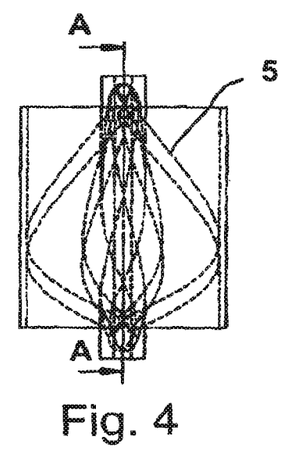
FIG. 4 a partly broken away side view of the subject of FIG. 1.

FIG. 4 shows a broken away representation of the rotor of FIG. 3, with the marginal regions 5 of the impeller blade 1 being shown in dashed form where it is connected to the sleeve/support device 4.

Figure 5:
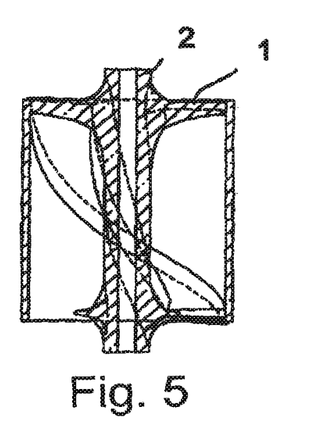
FIGS. 5 & 6 respective longitudinal sections of the subject of FIG. 1.

FIG. 5 shows a longitudinal section through the rotor of FIG. 1, with the impeller blade 1 intersecting the plane of the drawing at the upper end of the rotor.

Figure 6:
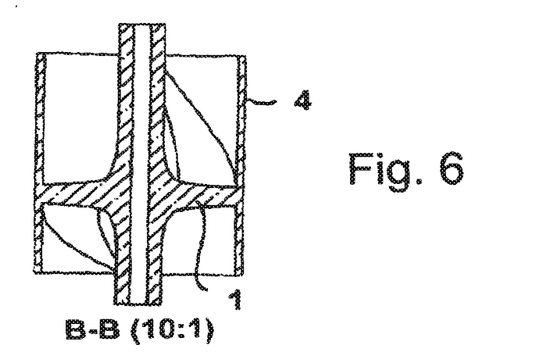

The impeller blade can, as shown in FIG. 5 and also in the following FIG. 6, be manufactured in one piece with the support device 4 made as a collapsible tube or as a collapsible pipe. Said support device can, for example, comprise a plastic as a flexible hose and can be held in an expanded and shape-stable manner by the pump action as a result of the overpressure built up in its interior. The shape stability can, however, also be established by the elastic restoring forces of the material. At the same time, the impeller blades are expanded and brought into the shape ready for operation by the expansion movement. The impeller blade 1, for example, is strained by tension and thus properly stabilized between the support device 4 and the neck 2 in the expanded state.

Figure 7:
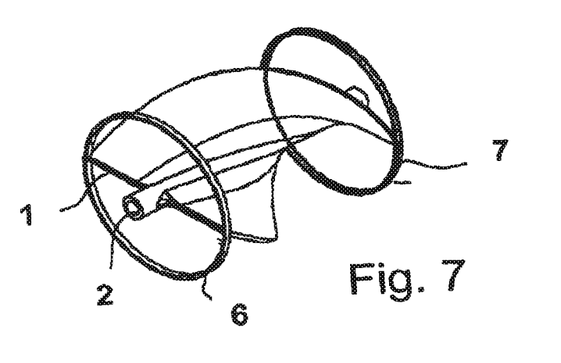
FIG. 7 a rotor with a support device comprising two rings and an impeller blade in a three-dimensional view.

An embodiment can be seen from FIG. 7 with two rings 6, 7 which together form the support device and support the impeller blade 1. The support regions of the impeller blade 1 in this respect lie radially of its furthermost margin.

The rings 6, 7 can comprise a shape memory alloy, nitinol, for example, and can be directly expanded after introduction into a body to adopt the shown circular shape. At the same time, they pull the support regions of the impeller blade 1 radially outwardly and tension it.

Figure 8:
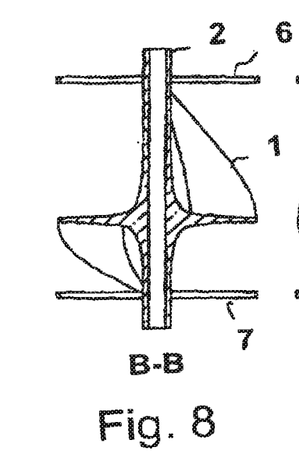
FIG. 8 the subject of FIG. 7 in a longitudinal section.
Figure 9:
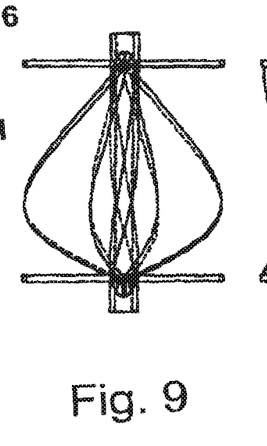
FIG. 9 the subject of FIG. 7 in a first side view.

FIG. 8 shows a longitudinal section through the rotor in accordance with FIG. 7 and FIG. 9 shows the extent of the margin of the impeller blade in a side view.

Figure 10:
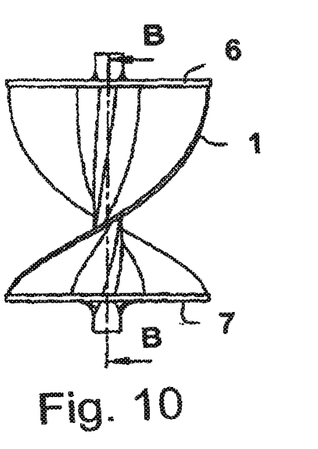
FIG. 10 the subject of FIG. 7 in a second side view.

FIG. 10 shows a three-dimensional side view which illustrates the helical structure of the impeller blade 1.

In addition to the elements shown, spacers can be provided between the rings 6, 7 which do not have to be shape-changeable and which can maintain their form on the transition between the compressed shape and the expanded shape of the rotor. They can be made as bars or braces extending parallel to the neck 2.

The rings 6, 7 can generally also comprise an elastic material, for example rubber-like material, which has small restoring forces on the transport to the point of use in compressed form and which stabilizes itself after adopting the circular ring shape.

Figure 11:
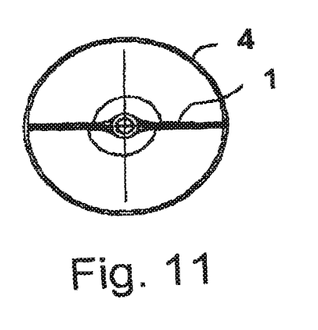
FIG. 11 the subject of FIG. 7 in an axial plan view.
Figure 12:
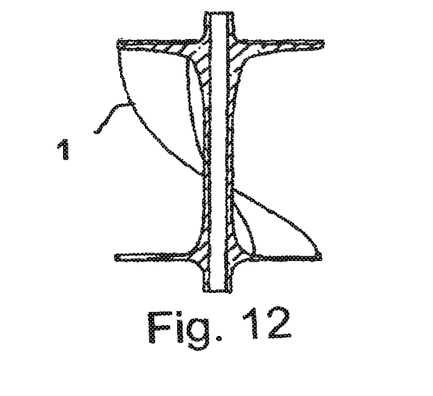
FIG. 12 the subject of FIG. 7 in a longitudinal section offset angle-wise with respect to the longitudinal section of FIG. 8.

FIG. 11 shows an axial plan view of the rotor in accordance with FIG. 7 and FIG. 12 shows a section in which the impeller blade 1 intersects the plane of the drawing at the upper and lower ends of the rotor. The impeller blade passes through 180 degrees of a helix between the upper end and the lower end of the rotor.

Figure 13:
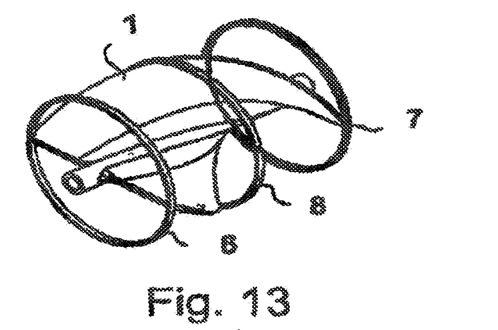
FIG. 13 a rotor with a support device comprising three rings.

A rotor of a fluid pump is shown in FIG. 13 which has a support device with three rings 6, 7, 8 which are each, viewed radially in the marginal region of the impeller blade 1, connected to it and can be spaced apart from one another by means of braces, not shown.

Figure 14:
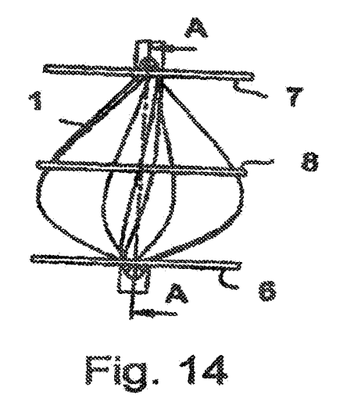
FIG. 14 a side view of the rotor of FIG. 13.

FIG. 14 shows a side view of the rotor of FIG. 13.

In FIG. 15, a rotor having four rings 6, 7, 8, 9 is shown perspectively, said rings together forming the major part of a support device. In another respect, what was already said with regard to the embodiments described above applies to the rings 6, 7, 8, 9.

Instead of individual rings, a helical body 7a can also be provided circumferentially at the periphery which is shown in dashed form in FIG. 15 and which is fastened spot-wise to the periphery of the impeller blade.

The torque can generally be introduced into the rotor via the support device. For this purpose, a part of the support device must, for example, be connected to a drive device or to a drive shaft via braces. This coupling will be looked at in more detail further below.

Alternatively, the torque can also be introduced via the neck 2 provided such a neck is present. In this case, the effect of the support device is restricted to the radial support and shape of the impeller blade/impeller blades.

Figure 16:
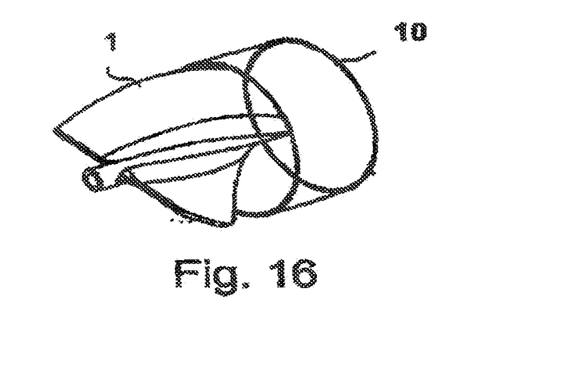
FIG. 16 a rotor in which the support: device comprises at least one tube piece.
Figure 17:
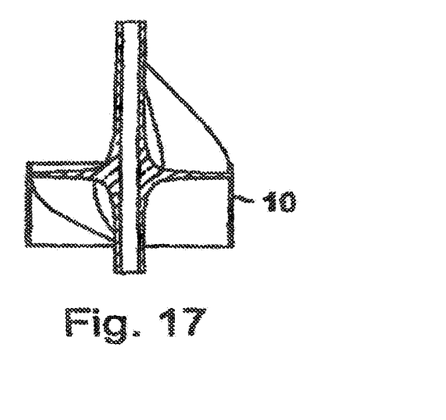
FIG. 17 a longitudinal section of the subject matter of FIG. 16.

FIG. 16 shows an embodiment in a three-dimensional representation in which an impeller blade 1 is stabilized at its periphery by a pipe section 10 or a tubular section. FIG. 17 shows the same arrangement in a longitudinal section.

The pipe section 10 can comprise a plastic, for example, and can be made in one piece with the impeller blade, but can also comprise a material different from the material of the impeller blade, for example a shape memory alloy. A tubular section or pipe section of this type has the disadvantage with respect to a ring of possibly being more difficult to compress, but has the advantage of being easy to stabilize in the expanded shape.

Figure 18:
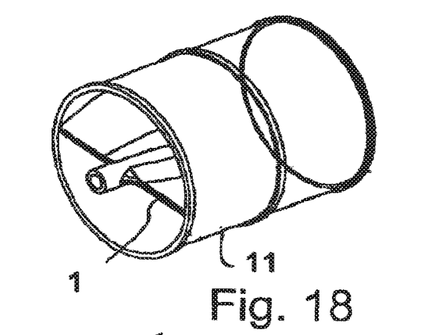
FIG. 18 a rotor in which the impeller blade/impeller blades are surrounded in full by a tubular support device, with reinforcement rings reinforcing the tube.

FIG. 18 shows, in a three-dimensional view, a rotor of a fluid pump having a rotor blade 1 which is supported by a support device 11 in the form of a throughgoing tube element. The tube element 11 extends across the complete axial length of the impeller blade. The tube element can, however, also be axially shorter than the impeller blade 1.

Figure 19:
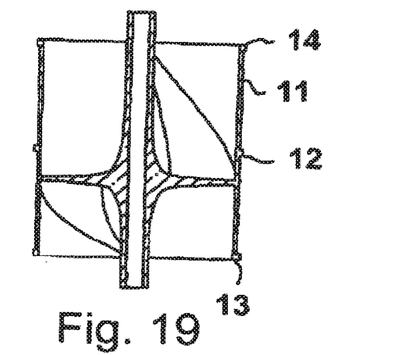
FIG. 19 the rotor of FIG. 18 in a longitudinal section.

FIG. 19 shows a longitudinal section through the embodiment of FIG. 18, with in particular three ring-like reinforcement elements 12, 13, 14 being able to be recognized which are fastened radially outwardly to the tube element 11 or are manufactured in piece therewith in a contiguous manner.

The reinforcement elements 12, 13, 14 can comprise the same material as the tube element 11, but can also comprise another material tending to be stiffer, for example a shape memory alloy of a rubber which may tend to be stiffer than the flexible material which the tube element 11 comprises.

In this respect, the tube element 11 can be at least partly co-expanded on the unfolding by expansion of the ring-shaped reinforcement elements 12, 13, 14. This expansion movement can moreover be reinforced by an overpressure built up in the rotor as soon as the rotor is set into rotation.

Figure 20:
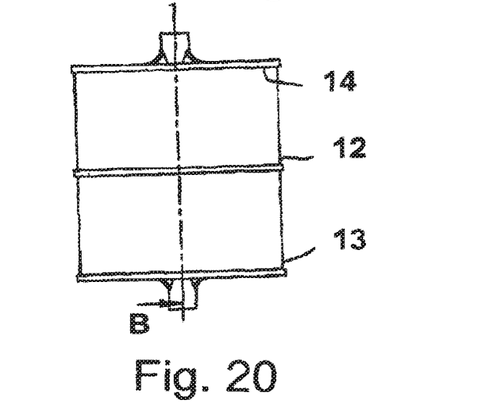
FIG. 20 the subject of FIG. 18 in a side view.

FIG. 20 shows a side view of the rotor of FIGS. 18, 19 in a closed form.

Figure 21:
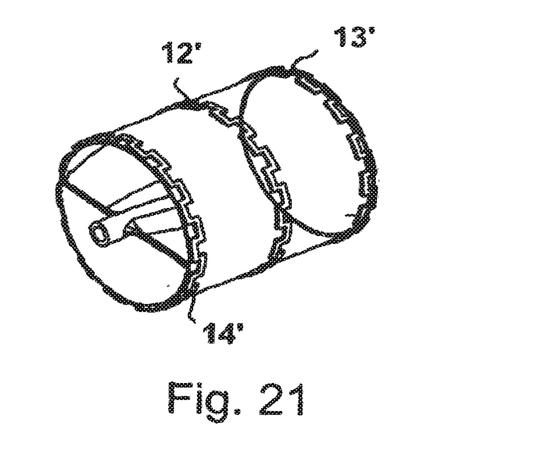
FIG. 21 the rotor of FIG. 18 in a three-dimensional view, with the support rings being designed in meandering form in the peripheral direction.

A variant is shown in FIG. 21 in which the ring-shaped reinforcement elements 12', 13', 14' are made in meandering form in the peripheral direction. These reinforcement elements can comprise a shape memory material and are particularly easily collapsible by the meander-like design. In addition to the rectangular meander-like structure shown, these reinforcement elements can also have a saw-tooth structure or a wavy-line structure.

Such reinforcement elements can be adhered to the tube element, for example.

Figure 22:
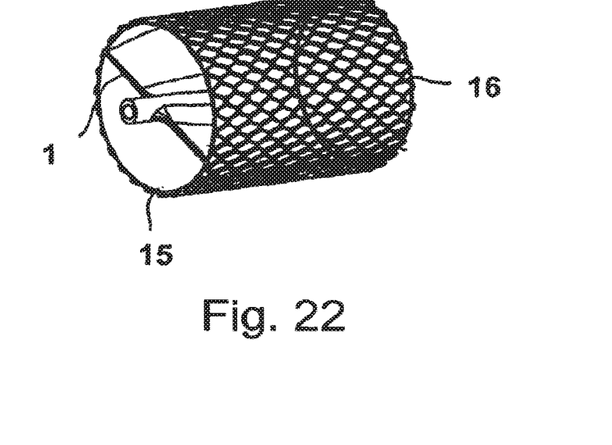
FIG. 22 a rotor with a tubular support device which is reinforced by a wire meshwork, in a three-dimensional view.

FIG. 22 shows, in a three-dimensional representation, a tube element 15 which forms a support device for the vane wheel 1 and is reinforced by wire meshwork 16 on its outer side. The wire meshwork 16 can be adhered, in particular also only spot-wise, to the tube element 15, for example. The wire meshwork can, as usual with stents, be made so that a radial compression does not result in a change in the length of the wire meshwork. The wire meshwork can comprise a shape memory alloy as a metal wire or also as a grid structure, in particular in one piece; however, a manufacture from a plastic is also conceivable.

Figure 23:
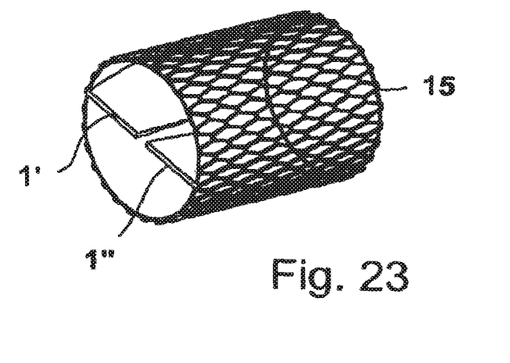
FIG. 23 a rotor similar to that of FIG. 22, with two rotor blades being arranged without a neck such that they do not extend up to the axis of rotation and can slide past one another on a compression of the rotor.

FIG. 23 shows an embodiment of a rotor having two impeller blades 1', 1" which are each helically fastened, for example adhesively bonded, at their outer sides in a tubular element 15, with the two helical shapes being matched to one another such that the two impeller blades 1', 1" being able to slide past one another radially with respect to the axis of rotation on compression of the support device 15 so that an extensive compression of the rotor is possible overall.

Both impeller blades 1', 1" end radially spaced apart from the axis of rotation, with a neck not being present. Only small forces act on the impeller blades at the margin of the rotor blades close to the axis of rotation due by the fluid to be conveyed since the relative movement is small in this region close to the axis. The space saved by omitting the neck can additionally be utilized for the transport of the fluid and the lack of the neck and the ability to push the impeller blades together makes an extensive compression of the rotor possible in the radial direction.

Figure 24:
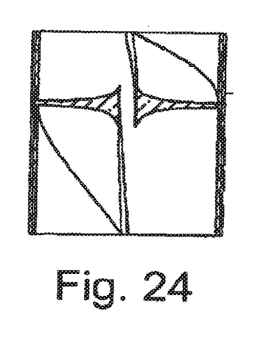
FIG. 24 the arrangement of FIG. 23 in a longitudinal section.

FIG. 24 shows the arrangement of FIG. 23 in a longitudinal section.

In a similar manner to the design of FIG. 22, the tubular sleeve which forms the support device for the impeller blades comprises an inner flexible sleeve and an outer wire meshwork.

FIGS. 25-29 in particular show the coupling of the support device to two shaft journals which are provided at both sides of the rotor and can serve both as a journalling and for the introduction of a torque.

Figures 25, 26, 27:
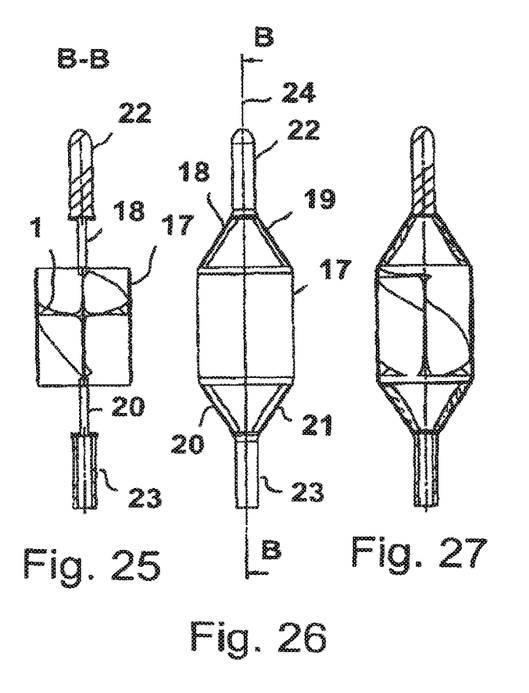
FIG. 25 a rotor arrangement with an impeller blade which is surrounded by a tubular support device, with the support device being connected at both sides to a respective shaft journal by means of fork-like braces.
FIG. 26 a side view of the subject of FIG. 25.
FIG. 27 a partly broken away view of the subject of FIG. 26.

FIG. 25 shows, in a longitudinal sectional representation, a tubular support device 17 which is connected via braces 18, 19, 20, 21 to two shaft journals 22, 23. Since the impeller blade 1 is supported by the support device 17, the total rotor is rotatably journalled and driven via the shaft journals 22, 23.

FIG. 26 shows a representation rotated by 90° about the axis of rotation 24 in a side view.

FIG. 27 shows a view from the same direction as FIG. 26 in a sectional representation.

Figure 28:
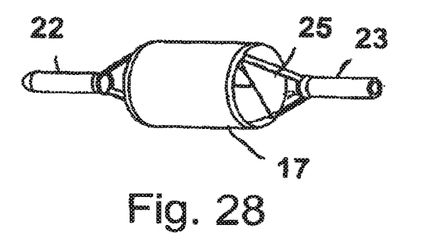
FIG. 28 a three-dimensional outer view of the subject of FIGS. 25-27.
Figure 29:
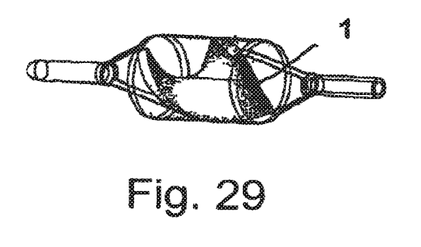
FIG. 29 a partly broken away three-dimensional view of the subject of FIG. 28.

FIGS. 28, 29 show respective three-dimensional representations of the subject of FIGS. 25, 26, 27, with FIG. 28 showing an outer view while FIG. 29 shows a partially broken away representation in which the impeller blade 1 becomes visible within the support device 17.

FIGS. 28, 39, unlike FIGS. 25, 26, 27, do not show fork-like braces 18, 19 as the connection between the support device 17 and the shaft journals 22, 23, but rather a triangular plate 25. It has the advantage with respect to two fork-like braces of being more stable, but the disadvantage that the fluid has to be displaced through the plate 25 on a rotational movement at high rotational frequency.

It becomes visible from FIG. 29 that a single helical impeller blade 1 is provided which has no neck.

Figure 30:
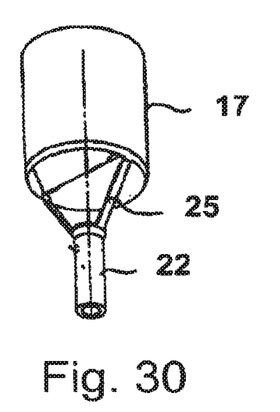
FIG. 30 a rotor with a tubular support device which is connected via a brace to a shaft journal, with a single impeller blade being provided.
Figure 31:
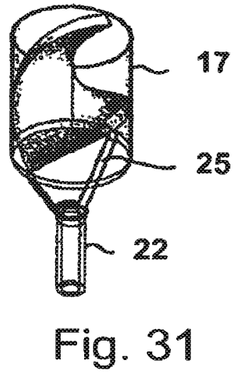
FIG. 31 the arrangement of FIG. 30 in a partly broken away view.

FIG. 30 shows a support device in which the torque is transmitted from the tubular element 17 into the shaft journal 22 by means of a triangular plate 25. FIG. 31 shows the same constellation in a partly broken away representation.

Figure 32:
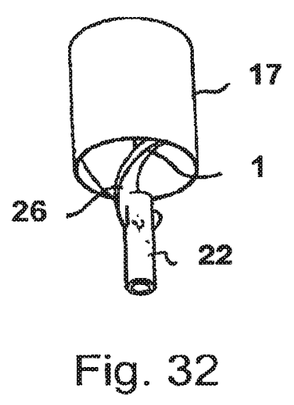
FIG. 32 an embodiment similar to the design of FIG. 30, with the impeller blade being coupled directly to the shaft journal and not via the support device.

In contrast to this, FIG. 32 shows the connection of the shaft journal 22 directly to a prolongation 26 of the impeller blade 1.

Figure 33:
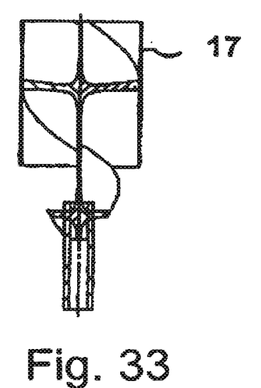
FIG. 33 the design of FIG. 32 in a longitudinal section.

FIG. 33 shows the same constellation as FIG. 32 in a longitudinal section. FIGS. 32 and 33 make clear that the torque is introduced directly into the impeller blade 1 there and that the support device 17 only serves the stabilization of the impeller blade/impeller blades radially in the outer region or the expansion of the impeller blade and the subsequent shape stabilization. The prolongation of the helical structure 26 up to the shaft journal 22 moreover has the advantage that this also causes less resistance in the surrounding fluid on rotation since it represents a prolongation of the helical structure of the impeller blade.

It was made clear by the above-described examples that a high stabilization of the impeller blades is achieved with a small effort with the means of the invention by the support of one or several impeller blades radially in their outer region. The connection of impeller blades to a neck is thereby either not particularly taken up or it becomes unnecessary in total, which can also result in the omission of the neck. The support device can moreover co-expand the rotor blade/rotor blades on the expansion of the rotor so that they can he manufactured from commercial, flexible materials without any particularly high mechanical demands.

The invention claimed is:

1. A fluid pump comprising:
a pump housing,
a rotor positioned within the pump housing, the rotor having an axis of rotation;
an impeller blade that extends radially in a direction from about the axis of rotation to an outer radial edge furthermost from the axis of rotation, has a compressed state and expanded state, and has a longitudinal length that extends within the pump housing, wherein the outer radial edge extends axially along the length of the blade, wherein the impeller blade is rotatable about the axis of rotation within the pump housing when in operation, and the rotor is configured to convey a fluid during operation; and
a support coupled to the outer radial edge of the impeller blade, wherein the support is coupled to the outer radial edge over a coupling length less than a total length of the outer radial edge, wherein the support is configured to pull the impeller blade radially outwardly.

2. The fluid pump of claim 1, wherein the support at least partly surrounds the at least one impeller blade.

3. The fluid pump of claim 1, wherein the rotor further comprises a hub, and wherein the impeller blade extends radially from the hub.

4. The fluid pump of claim 1, wherein the coupling length comprises a plurality of coupling lengths along the outer radial edge, wherein a sum of the plurality of coupling lengths is less than the total length of the outer radial edge.

5. The fluid pump of claim 1, wherein the support comprises a shape memory alloy.

6. The fluid pump of claim 1, wherein the support comprises an elastic material.

7. The fluid pump of claim 1, wherein the support is changeable between a first state in which the support is radially compressed associated with the compressed state of the rotor and a second state in which the support is radially expanded associated with the expanded state of the rotor.

8. The fluid pump of claim 1, wherein a majority of a surface area of the impeller blade conveying the fluid extends radially inward from the support.

9. The fluid pump of claim 1, wherein the impeller blade is connected to the support and said support rotates with the impeller blade.

10. The fluid pump of claim 1, wherein the support comprises a ring with a meandering form in the peripheral direction.

11. The fluid pump of claim 1, wherein the support is configured as two or more mutually axially spaced apart rings.

12. A fluid pump in accordance with claim 1, wherein the support is configured as a flexible tube at least partly surrounding the impeller blade.

13. The fluid pump of claim 12, wherein the flexible tube is inflatable and stable in shape in pumping operation.

14. The fluid pump of claim 1, wherein all components of the impeller blade are radially spaced apart from the axis of rotation.

15. The fluid pump of claim 1, wherein the fluid pump has a constant diameter in the region of the impeller blade.

16. The fluid pump of claim 1, wherein the support comprises a wire meshwork compressible in diameter.

17. The fluid pump of claim 1, wherein the support is fixedly coupled to the impeller blade.

18. The fluid pump of claim 1, wherein the support comprises a helical structure at least partly surrounding the impeller blade.

19. The fluid pump of claim 18, wherein the impeller blade comprises a helical blade.

20. The fluid pump of claim 19, wherein a first helical direction of the helical structure is opposite a second helical direction of the helical blade.

21. The fluid pump of claim 19, wherein a first helical direction of the helical structure is in a same direction as a second helical direction of the helical blade.

* * * * *